United States Patent [19]

Stewart et al.

[11] Patent Number: 5,948,649
[45] Date of Patent: Sep. 7, 1999

[54] METHOD FOR IDENTIFYING NUCLEIC ACID SEQUENCES FROM DIFFERENT BIOLOGICAL SOURCES THROUGH AMPLIFICATION OF THE SAME

[75] Inventors: Gordon Sydney Anderson Birnie Stewart, Loughborough; Kevin Patrick Francis, Lincoln, both of United Kingdom

[73] Assignee: Biotec Laboratories Limited, Suffolk, United Kingdom

[21] Appl. No.: 08/666,493

[22] PCT Filed: Nov. 13, 1995

[86] PCT No.: PCT/GB95/02654

§ 371 Date: Jul. 11, 1996

§ 102(e) Date: Jul. 11, 1996

[87] PCT Pub. No.: WO96/15264

PCT Pub. Date: May 23, 1996

[30] Foreign Application Priority Data

Nov. 12, 1994 [GB] United Kingdom .................... 9422891

[51] Int. Cl.⁶ ................................ C12P 19/34; C12Q 1/68
[52] U.S. Cl. ................................. 435/91.2; 435/6
[58] Field of Search ................... 435/91.2, 810; 536/25.32, 23.7, 24.3

[56] References Cited

U.S. PATENT DOCUMENTS 4,965,188 10/1990 Mullis et al. ............................... 435/6
5,470,971 11/1995 Kondo et al. ........................... 536/23.7

FOREIGN PATENT DOCUMENTS

92/05277 4/1992 WIPO .

OTHER PUBLICATIONS

Jiang et la. Chloramphenicol induces the transcription of the major cold shock gene of *Escherichia coli*, cspA J. Bacteriology, vol. 175 (18), pp. 5824–5828), 1993.

*Primary Examiner*—Eggerton A. Campbell
*Attorney, Agent, or Firm*—Wenderoth, Lind & Ponack, L.L.P.

[57] ABSTRACT

A method of identifying a nucleic acid sequence in a biological sample comprises using a pair of universal oligonucleotide primers to amplify the nucleic acid sequence and characterizing the amplification reaction products. Preferred universal primers are derived from conserved regions of cold shock or Y-box proteins and hybridize to the genes that code for the peptide sequences GXVKWFNXXKGF-GFI and GPXAXNVTXX.

17 Claims, 3 Drawing Sheets

```
                    MSGKMTGIVKWFNADKGFGFITPDDGSKDVFVHFSAIQN
E.c   CspA          --N-----L-------------S-V-------------G
E.c   CspB          -:A-IK-Q------ES-----------A----------G
E.c   CspC          -:::EK-T------NA-------C-EG-GE-I-A-Y-T--M
E.c   CspD          -:::LE-K------SE-----EV-E-QD----------G
B.s   CspB          -------------SE--L---EV-E-QD----------G
B.g   CspBgl        -------------I-------EV-E-QD----------G
B.gl  CspBgs        -------------SE------EV-E-QD----------G
B.c   CspBca        -:::QR-K------NE--Y--EVEG---:-----T---G
B.st  CspBst        -:::QR-K------NE--Y--EVEG---:-----T---G
S.c   SC7.0         -:::A--T------E------AQ-G-GP------Y---NA
H.s   YB-1          IAT-VL-T------VRN-Y--NRN-TKE------QT--KK
R.n   EFI           IAT-VL-T------VRN-Y--NRN-TKE------QT--KK
X.l   FRGY-1        IAT-VL-T------VRN-Y--NRN-TKE------QT--KK
A.t   GRP-2         GGERRK-S------DTQ---------GD-L----Q-S-RS

:::DGYKSLDEGQKVSFTI:ESGAKGPAAGNVTSL
E.c   CspA          :::::-N-RT-F----T-S-:-------A--IITD
E.c   CspB          :::::N-F-T-A--N-E-E-:QD-Q----V---AI
E.c   CspC          :::::---RT-KA--S-Q-DV:EQ-P--NH-SVIVPVEVEVAAVA
E.c   CspD          :::::E-F-T-E---A----E-:VE-NR--Q-A---KEA
B.s   CspB          :::::E-F-T-ES--A----E-:VE-NR--Q-A
B.g   CspBgl        :::::E-F-FCT-E--A----E-:VE-NR--Q-A
B.gl  CspBgs        :::::E-F-T-EA--A----E-:VE-NR--Q-A
B.c   CspBca        :::::E-F-T-E---EA----EQ:VE-NR--Q-AV-L
B.st  CspBst        :::::E-FST-E--EA----EQ:VE-NR--Q-AV-L
S.c   SC7.0         :::::T-FR--E-N-V-N-DV:TB-E:--Q-E--SPA
H.s   YB-1          NNPRKYLR-VGD-ET-E-DV:VE-E--EE-A---GPG
R.n   EFI           NNPRKYLR-VGD-ET-E-DV:VE-E--AE-A---GPG
X.l   FRGY-1        NNPRKYLR-VGD-ET-E-DV:VE-E--AE-A---GPG
A.t   GRP-2         :::E-FR--AAEE--E-EVEIDN-NR-K-ID-SGPD
```

```
FRONT   E. c cspA   GGTATCGTAAAATGGTTCAACGC   20/23 (SEQ ID NO: 8)
        E. c cspB   GGTTTAGTAAAATGGTTTAACGC   21/23 (SEQ ID NO: 9)
        E. c cspC   GGTCAGGTTAAGTGGTTCAACGA   17/23 (SEQ ID NO: 10)
        S. t cspS   GGTATCGTAAAATGGTTCAACGC   20/23 (SEQ ID NO: 11)
        S. t cspB   GGTTTAGTAAAATGGTTTAACCC   20/23 (SEQ ID NO: 12)
        B. s cspB   GGTAAAGTAAAATGGTTCAACTC   21/23 (SEQ ID NO: 13)
        L. m cspL   GGTACAGTAAAATGGTTTAACGC   22/23 (SEQ ID NO: 14)
        P. m cspP   GGAAAAGTAAAATGGTTTAACGC   22/23 (SEQ ID NO: 15)
        FRG Y1      GGGACAGTCAAATGGTTTAATGT   18/23 (SEQ ID NO: 16)

UNI         GGtaaaGTaAAaTGGTTtAAcgc  FAM (SEQ ID NO: 17)

MIDDLE  E. c cspA   GATGTATTCGTTCATTTCTCTGCTATTC   26/28 (SEQ ID NO: 18)
        E. c cspB   GATGTGTTTGTGCATTTTTCTGCGATTC   22/28 (SEQ ID NO: 19)
        E. c cspC   GATGTGTTCGTACACTTCTCCGCTATCC   25/28 (SEQ ID NO: 20)
        S. t cspS   GATGTGTTCGTACACTTCTCTGCTATTC   25/28 (SEQ ID NO: 21)
        S. t cspB   GATGTGTTCGTACACTTCTCTGCTATCC   26/28 (SEQ ID NO: 22)
        B. s cspB   GATGTATTCGTTCATTTCTCTGCTATTC   26/28 (SEQ ID NO: 23)
        L. m cspL   GATGTATTCGTACATTTCAGCGCTATCC   25/28 (SEQ ID NO: 24)
        P. m cspP   GATGTATTCGTTCACTTCTCAGCTACTC   23/28 (SEQ ID NO: 25)
        FRG Y1      GATGTGTTTGTACACCAAACTGCCATCA   19/28 (SEQ ID NO: 26)

UNI         GATGTaTTcGTaCAtttctctGCtAtcc  TAMRA (SEQ ID NO: 27)

BACK    E. c cspA   GGCCCGGCAGCTGGTAACGTAACC   19/24 (SEQ ID NO: 28)
        E. c cspB   GGTCCTGCAGCAGCAAATGTCATC   18/24 (SEQ ID NO: 29)
        E. c cspC   GGTCCGGCAGCTGTTAACGTAACA   18/24 (SEQ ID NO: 30)
        S. t cspS   GGCCCGGCAGCTGGTAACGTAACC   19/24 (SEQ ID NO: 31)
        B. s cspB   GGACCACAAGCTGCTAACGTTACT   19/24 (SEQ ID NO: 32)
        L. m cspL   GGACCTCAAGCAGCTAACGTTCAA   19/24 (SEQ ID NO: 33)
        FRG Y1      GGTGCAGAGGCAGCTAATGTAACT   18/24 (SEQ ID NO: 34)

UNI         GGacCtgaaGCaGctAAcGTAacc   JOE (SEQ ID NO: 35)
```

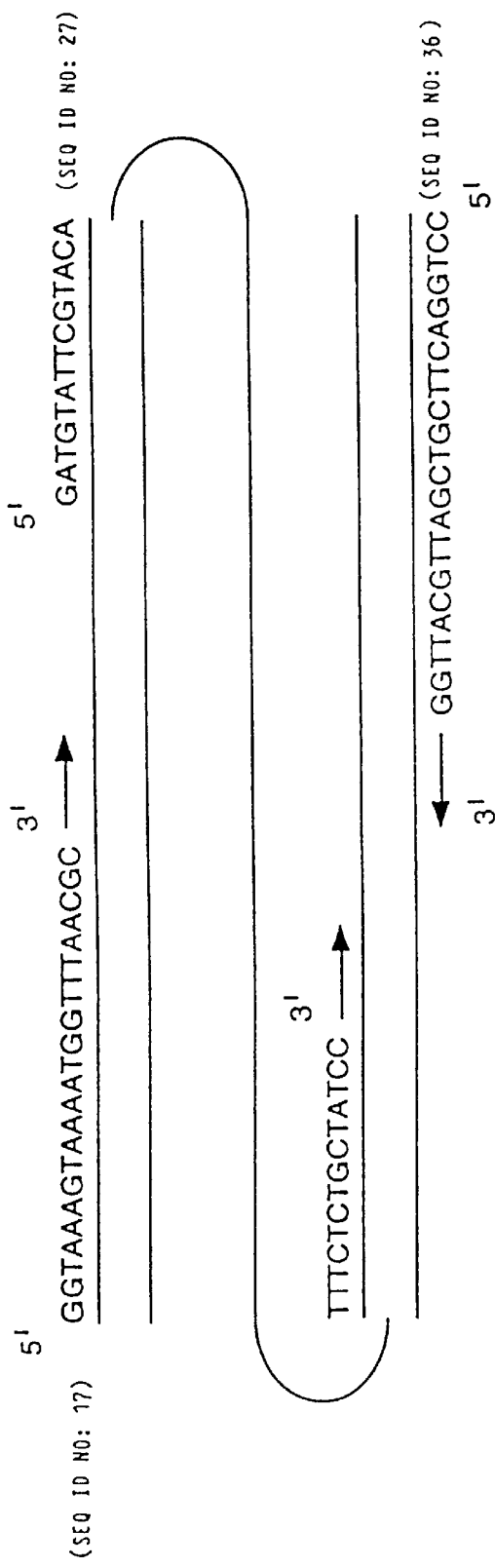

```
                           SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Gly Xaa Val Lys Trp Phe Asn Xaa Xaa Lys Gly Phe Gly Phe Ile
1               5                  10                  15

(2) INFORMATION FOR SEQ ID NO:2:

(i) SEQUENCE CHARACTERISTICS:
         (A) LENGTH: 23 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

GGTANAGTAA AATGGTTNAA CNC                                              23

(2) INFORMATION FOR SEQ ID NO:3:

(i) SEQUENCE CHARACTERISTICS:
         (A) LENGTH: 10 amino acids
         (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO:3:

Gly Pro Xaa Ala Xaa Asn Val Thr Xaa Xaa
1               5                   10

(2) INFORMATION FOR SEQ ID NO:4:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGTTACGTTA NCNGCTNNNG GNCC                                              24

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asp Val Phe Val His Phe Ser Ala Ile Gln
1               5                   10

(2) INFORMATION FOR SEQ ID NO:6:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATGTATTCG TACATTTCTC TGCTATCC                                          28

(2) INFORMATION FOR SEQ ID NO:7:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGATAGCAGA GAAATGTACG AATACATC                                          28

(2) INFORMATION FOR SEQ ID NO:8:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGTATCGTAA AATGGTTCAA CGC                                                    23

(2) INFORMATION FOR SEQ ID NO:9:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GGTTTAGTAA AATGGTTTAA CGC                                                    23

(2) INFORMATION FOR SEQ ID NO:10:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

GGTCAGGTTA AGTGGTTCAA CGA                                                    23

(2) INFORMATION FOR SEQ ID NO:11:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

GGTATCGTAA AATGGTTCAA CGC                                                    23

(2) INFORMATION FOR SEQ ID NO:12:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GGTTTAGTAA AATGGTTTAA CCC                                                    23

(2) INFORMATION FOR SEQ ID NO:13:

(i) SEQUENCE CHARACTERISTICS:
            (A) LENGTH: 23 bases
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GGTAAAGTAA AATGGTTCAA CTC                                                    23

(2) INFORMATION FOR SEQ ID NO:14:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGTACAGTAA AATGGTTTAA CGC                                                  23

(2) INFORMATION FOR SEQ ID NO:15:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGAAAAGTAA AATGGTTTAA CGC                                                  23

(2) INFORMATION FOR SEQ ID NO:16:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGACAGTCA AATGGTTTAA TGT                                                  23

(2) INFORMATION FOR SEQ ID NO:17:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGTAAAGTAA AATGGTTTAA CGC                                                  23

(2) INFORMATION FOR SEQ ID NO:18:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GATGTATTCG TTCATTTCTC TGCTATTC                                             28

(2) INFORMATION FOR SEQ ID NO:19:

(i) SEQUENCE CHARACTERISTICS:

(A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GATGTGTTTG TGCATTTTTC TGCGATTC                                        28

(2) INFORMATION FOR SEQ ID NO:20:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GATGTGTTCG TACACTTCTC CGCTATCC                                        28

(2) INFORMATION FOR SEQ ID NO:21:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GATGTGTTCG TACACTTCTC TGCTATTC                                        28

(2) INFORMATION FOR SEQ ID NO:22:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GATGTGTTCG TACACTTCTC TGCTATCC                                        28

(2) INFORMATION FOR SEQ ID NO:23:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GATGTATTCG TTCATTTCTC TGCTATTC                                        28

(2) INFORMATION FOR SEQ ID NO:24:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GATGTATTCG TACATTTCAG CGCTATCC                                               28

(2) INFORMATION FOR SEQ ID NO:25:

(i) SEQUENCE CHARACTERISTICS:
         (A) LENGTH: 28 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:25:

GATGTATTCG TTCACTTCTC AGCTACTC                                               28

(2) INFORMATION FOR SEQ ID NO:26:

(i) SEQUENCE CHARACTERISTICS:
         (A) LENGTH: 28 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:26:

GATGTGTTTG TACACCAAAC TGCCATCA                                               28

(2) INFORMATION FOR SEQ ID NO:27:

(i) SEQUENCE CHARACTERISTICS:
         (A) LENGTH: 28 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:27:

GATGTATTCG TACATTTCTC TGCTATCC                                               28

(2) INFORMATION FOR SEQ ID NO:28:

(i) SEQUENCE CHARACTERISTICS:
         (A) LENGTH: 24 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:28:

GGCCCGGCAG CTGGTAACGT AACC                                                   24

(2) INFORMATION FOR SEQ ID NO:29:

(i) SEQUENCE CHARACTERISTICS:
         (A) LENGTH: 24 bases
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:29:

GGTCCTGCAG CAGCAAATGT CATC                                                   24

(2) INFORMATION FOR SEQ ID NO:30:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGTCCGGCAG CTGTTAACGT AACA                                      24

(2) INFORMATION FOR SEQ ID NO:31:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGCCCGGCAG CTGGTAACGT AACC                                      24

(2) INFORMATION FOR SEQ ID NO:32:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GGACCACAAG CTGCTAACGT TACT                                      24

(2) INFORMATION FOR SEQ ID NO:33:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGACCTCAAG CAGCTAACGT TCAA                                      24

(2) INFORMATION FOR SEQ ID NO:34:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

GGTGCAGAGG CAGCTAATGT AACT                                      24

(2) INFORMATION FOR SEQ ID NO:35:

(i) SEQUENCE CHARACTERISTICS:

```
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GGACCTGAAG CAGCTAACGT AACC                                              24

(2) INFORMATION FOR SEQ ID NO:36:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CCTGGACTTC GTCGATTGCA TTGG                                              24

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Gly Xaa Val Lys Trp Phe Asn Xaa Xaa Gly Gly Phe Gly Phe Ile
1               5                   10                  15

(2) INFORMATION FOR SEQ ID NO:38:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Gly Pro Xaa Ala Xaa Asn Val Thr Xaa Xaa
1               5                   10
```

METHOD FOR IDENTIFYING NUCLEIC ACID SEQUENCES FROM DIFFERENT BIOLOGICAL SOURCES THROUGH AMPLIFICATION OF THE SAME

This Application is a 371 of PCT/GB95/02654, Nov. 13, 1995.

BACKGROUND OF THE INVENTION

1. Field of the Invention

The present invention relates to improvements in and relating to the amplification and identification of nucleotide base sequences, and in particular but not exclusively to improvements in and relating to the amplification and identification of nucleotide base sequences using the polymerase chain reaction (PCR).

2. Description of the Related Art

The PCR is a useful technique for amplifying genetic sequences. One application of this is the amplification of target gene sequences in biological samples from, for example, environmental, food and medical sources, etc. to allow identification of causative, pathogenic, spoilage or indicator organisms present in the sample.

Conventionally, the PCR is carried out using primers chosen or produced to amplify a particular target gene sequence within a given organism. Consequently, currently the PCR can only be used to amplify a single predetermined gene sequence at any one time and hence to confirm the presence or absence of that target sequence and the corresponding organism. Thus, when the identity of one or more organisms in a sample is to be established, it is necessary to guess or assume what sequences/organisms may be present, identify and obtain specific primers that are operable to amplify that sequence or a sequence indicative of that organism, and then conduct the experiment. Such procedures are time consuming and expensive, and somewhat unreliable.

It is an object of the present invention to obviate or mitigate one or more of the above disadvantages.

SUMMARY OF THE INVENTION

Throughout this specification the terms "unidentified sequence" and "unidentified nucleotide sequence" are used to mean that the sequence has not yet been identified in the particular sample being analysed, not necessarily one which is wholly unknown. It may be that once an unidentified sequence has been amplified and characterised it is one with which scientists are familiar.

In one aspect the invention provides a method of identifying a nucleic acid sequence in a biological sample, which method comprises using at least one pair of oligonucleotide primers to amplify the nucleic acid sequence, and characterising the amplification reaction products, characterised in that the or each pair of oligonucleotide primers is operable to enable the amplification of nucleic acid sequences from different biological sources.

The amplification method is not material to the invention. Preferably amplification is effected by the polymerase chain reaction (PCR).

The method by which amplification reaction products are characterised is also not material to the invention. Such characterisation may be effected by known techniques, e.g. sequencing, or by the use of single-strand conformation polymorphism (SSCP) analysis, or by the use of a labelled probe which binds to the amplification reaction products.

One suitable system is that marketed by Perkin Elmer under the trademark TaqMan which is described in more detail below.

The method of the invention is characterised by the use of at least one pair of oligonucleotide primers operable to enable the amplification of nucleic acid sequences from different biological sources. These so-called universal primers can be selected from regions of genes which are largely or completely conserved in many different biological organisms. Pairs of universal primers may be found by routine search in various different genes. To the best of the inventors' knowledge, the use of such pairs of universal primers in order to identify the biological source of a particular nucleic acid sequence has not previously been proposed.

In another aspect the invention provides a kit for identifying a nucleic acid sequence in a biological sample by the method described which kit comprises reagents, including at least one pair of oligonucleotide primers operable to enable the amplification of nucleic acid sequences from different biological sources, for amplifying the nucleic acid sequence, and means for characterising the amplification reaction products.

Studies have revealed that the proteins involved in the cold-shock response in prokaryotic organisms are remarkably conserved throughout different organisms. Such conservation also extends to related proteins in eukaryotic organisms, for example the Y-box proteins. Very highly conserved regions of the amino acid sequences of these proteins have been identified, and recognised by the inventors as potential sites for universal amplification primers.

Preferably a pair of oligonucleotide primers includes a first oligonucleotide primer which is substantially complementary to a nucleic acid sequence that codes for the peptide sequence GXVKWFNXXKGFGFI (SEQ ID NO: 1) where X is any amino acid, or for a fragment thereof that includes at least four identified amino acids.

Herein, peptide sequences are shown in the N to C terminus direction. Oligonucleotides are shown in the 5' to 3' direction. Reference to an amino acid in a peptide sequence is to be understood as a reference to the residue of that amino acid. Reference to a nucleotide in an oligonucleotide sequence is to be understood as a reference to a residue of that nucleotide. An identified amino acid is one not indicated by the symbol X.

Preferably the said first oligonucleotide primer has the sequence GGTANAGTAAAATGGTTNAACNC (SEQ ID NO: 2) where N is any nucleotide, or a fragment thereof containing at least twelve nucleotides.

Preferably a second oligonucleotide primer is substantially complementary to a nucleic acid sequence that codes for the peptide sequence GPXAXNVTXX (SEQ ID NO: 3) where X is any amino acid, or for a fragment thereof that includes at least four identified amino acids. Preferably the said second oligonucleotide primer has the sequence GGTTACGTTANCNGCTNNNGGNCC (SEQ ID NO: 4) where N is any nucleotide, or a fragment thereof containing at least twelve nucleotides.

Preferably a third oligonucleotide primer used is substantially complementary to a nucleic acid sequence that codes for the peptide sequence DVFVHFSAIQ (SEQ ID NO: 5). Preferably the said third oligonucleotide primer used has the sequence GATGTATTCGTACATTTCTCTGCTATCC (SEQ ID NO 6) or its reverse complement GGATAGCAGAGAAATGTACGAATACATC (SEQ ID NO: 7) or a fragment of either containing at least twelve nucleotides or an oligonucleotide having at least 80% homology therewith.

The third oligonucleotide primer or its reverse complement forms a pair with either the second or the first oligonucleotide primers, respectively. Alternatively, the first oligonucleotide primer forms a pair with the second oligonucleotide primer.

In another aspect the invention provides as new products, a pair of oligonucleotide primers comprising the first and one of the other two oligonucleotides, and a pair of oligonucleotide primers comprising the second and third oligonucleotides, and a set of primers comprising all three oligonucleotides.

BRIEF DESCRIPTION OF THE FIGURES

Reference is directed to the accompanying drawings in which

FIG. 1 is a comparison of the aligned amino acid sequences of the major cold shock proteins of various bacteria and of a number of eukaryotic Y-box proteins.

FIG. 2 shows the sequences of three conserved regions of genes which code for these proteins, and includes three oligonucleotides whose sequences or reverse complementary sequences are suitable for use as primers according to this invention.

FIG. 3 is a schematic representation of an oligonucleotide primer set in use in the amplification of a nucleic acid sequence according to this invention.

FIGS. 4 and 5 show the front and back oligonucleotide primers from FIG. 2, and how they relate to conserved peptide sequences of cold shock and Y-box proteins.

More specifically FIG. 1 shows alignments of amino acid sequences of published cold shock and Y-box proteins. (:=space in sequence; -=conserved amino acid). E.c=*Escherichia coli*, B.s=*Bacillus subtilis*, B.g=*Bacillus globigii*, B.gl=*Bacillus globisporus*, B.c=*Bacillus caldolyticus*, B.st=*Bacillus stearothermophilus*, S.c=*Streptomyces calvuligers*, H.s=*Homo sapiens*, R.n=*Rattus norvegicus*, X.l=*Xenopus laevis*, A.t=*Arabidopsis thaliana*. The data clearly demonstrates that these proteins share large regions of homology. By identifying the most highly conserved regions within these alignments, oligonucleotide primers were designed which, when used in a PCR reaction using chromosomal DNA from various bacteria, facilitate the amplification of short DNA sequences (~180 bp) possessing regions of homology with published major cold shock protein sequences.

FIG. 2 focuses on three highly conserved regions of FIG. 1, and shows how the genes which code for these proteins are also highly conserved, both across various bacterial species and also in the frog. These conserved regions have been used to design three degenerate primers;

a first or front primer which hybridises to the active coding strand of the DNA;

a middle or third oligonucleotide which hybridises to the coding or the non-coding strand of the DNA; and a back or second primer which hybridises to the non-coding strand of the DNA.

In these degenerate oligonucleotides, a capital letter designates a nucleotide that is conserved throughout; a small letter designates a nucleotide that is not universally conserved; and a dot indicates that the nucleotide shown below it can be changed at will.

The three oligonucleotides shown in FIG. 3 are indeed universal primers. Using them, the inventors have successfully amplified DNA sequences in biological samples derived from bacteria, eukaryotes including rat, frog and man, and plant tissue. For example, nucleic acid sequences have been amplified from the following micro-organisms:

*Bacillus subtilis*
*Xanthomonas campestris*
*Salmonella typhimurium*
*Micrococus luteus*
*Chromobacterium violaceum*
*Agrobacterium tumefaciens*
*Azospirillus*
*Rahnella aquaticus*
*Pseudomonas putida*
*Serratia liquifaciens*
*Serratia marcescens*
*Pseudomonas fluorescens*
*Staphylococcus aureus*
*Pseudomonas aeruginosa*
*Pseudomonas mesoacidophilus*
*Photobacterium leiognathi*
*Vibrio fischeri*
*Xenorhabdus luminescens*
*Listeria monocytogenes*
*Bacillus stearothermophilus*
*Thermophilus aquaticus*
*Yersinia enterocolitica*

Amplification was performed under conventional PCR conditions, using a touchdown technique to minimise interference from impurities. The following temperature profile was used:

a) 94° C. for 6 minutes.
b) 94° C. for 30 seconds.
   60–51° C. for 30 seconds.
   72° C. for 30 seconds.
   b) repeated 20 times with the annealing temperature reduced by one degree every second cycle.
c) 94° C. for 30 seconds
   50° C. for 30 seconds
   72° C. for 30 seconds
   c) cycle repeated 20 times.

FIG. 3 shows front and middle primers of FIG. 2 hybridised to the coding strand of a nucleic acid, and the reverse complement back primer from FIG. 2 hybridised to the non-coding strand of the DNA. The front and back primers form a pair of oligonucleotide primers according to the invention. The middle and back primers form another pair of oligonucleotide primers. The three primers together form a set according to the invention.

FIG. 4 shows the highly conserved amino acid sequence of the cold shock proteins used to produce the front primer of the primer pair. FIG. 5 shows the highly conserved peptide sequence of the cold shock proteins used to produce the back primer of the primer pair. Each X in the sequence indicates a position in the sequence at which the precise nature of the amino acid is not particularly important since these positions are less conserved than the others. Consequently the nature of the primer at the corresponding position can vary without detriment to the efficacy of the respective primer.

FIG. 4 also shows the front oligonucleotide primer of the universal primer pair, alongside the particularly conserved peptide sequence from which it is derived. It should be noted that the conservation of the peptide sequence is greater than that of the corresponding nucleotide sequence due to "wobble", i.e. amino acids can be coded for by more than one codon triplet. Thus, the primer is one of a number of possible primers that are hybridisable to the DNA sequence actually coding for the conserved sequence GXVKW-FNXXKGFGFI (SEQ ID NO: 1). This primer is complementary to and hence operable to hybridise to a first primer binding region on the coding or sense strand of a cold shock protein gene sequence, as shown in FIG. 3.

FIG. 5 shows the back oligonucleotide primer of the pair, alongside the highly conserved peptide sequence from which it is derived. The back primer is operable to hybridise with a second primer binding region on the noncoding or anti-sense strand of a cold shock protein gene sequence, again as shown in FIG. 3.

DETAILED DESCRIPTION OF THE INVENTION

The primer binding regions are separated by a generally less conserved series of about 180 base pairs. This less well conserved part of the gene encodes for a cold-shock response protein, or a related or similar protein such as a Y-box protein (eukaryotes). The primer binding regions are sufficiently conserved to enable the universal primers to recognise and hybridise to the DNA of a large number, possibly all or almost all, organisms, including both prokaryotic and eukaryotic organisms and thereby enable amplification of the intervening sequences from these organisms as will be described. The primer pair is at least expected to operate with very large classes of organisms and thus to be "universal" in this sense. The gene however does have a degree of peculiarity in each different type of organism, such that characterisation of the amplification products made with the primers and identification of the sequence, the RNA, protein and source organism can be made (see later).

In use, the primers are operable in a generally conventional polymerase chain reaction to amplify a gene encoding for a cold shock or related protein or indeed any sequence bounded by the highly conserved primer binding regions. It is preferable that the reaction is conducted using a substantially DNA free thermophilic transcription enzyme to mitigate "background" amplification i.e. amplification of exogenous DNA associated with the enzyme. However, use of an improved polymerase chain reaction method in accordance with the present invention may render this requirement less crucial (see below). A suitable enzyme is replitherm.

One particular application of the universal primer pair is the identification of unidentified source organisms in a biological sample. For example, food, environmental and medical samples can be analysed to identify the nature of a particular causative, pathogenic spoilage and/or indicator organism.

Conventionally sequence specific and hence organism-specific primers have had to be chosen or produced to enable such identification procedures. One significant disadvantage of this, which the present invention obviates, is the need for the investigator to guess or assume what organism may be involved, and test for it. If that organism is not involved, then the investigator will have to guess again. This has to be repeated until the investigator has correctly guessed or assumed the identity of the organism involved and the test has proved this to be the case. It is feasible that the organism involved is not identified as a result of such laborious techniques. Moreover, it may be that more than one organism is involved, a fact that may be missed using conventional techniques, but which should not be missed using the present invention.

The present invention allows an investigator simply to conduct the polymerase chain reaction using the universal primers to amplify all sequences present in the sample bound by the relevant highly conserved primer binding regions. The polymerase reaction products (the amplified sequences) can then be characterised, for instance by sequencing them or using high resolution gel electrophoresis, to enable identification of the sequence amplified. It is preferable that techniques are adopted which obviate the need to sequence the amplification products, since sequencing is a relatively laborious process.

Therefore, in accordance with the present invention the gel pattern produced using electrophoretic techniques to separate the reaction products produced using the primers may be compared against a data bank of gel patterns produced from known sequences and organisms, such that identification of the sequence and hence source organism in the sample being analysed can be readily ascertained by matching it with one in the data bank. If there is no corresponding pattern on the data bank then the products may have to be sequenced, or identified by another appropriate method. It will be appreciated that determination of the identity of the sequence and source organism by such comparative procedures is highly efficient, particularly when the comparison is conducted by a computer.

The use of fluorescent labels to label the PCR products facilitates the identification procedure.

The front and back and middle primers may be labelled with fluorescent labels (FIG. 3; e.g. FAM, TAMRA, JOE as shown in FIG. 2). Thus, when the reaction products are separated on a gel, the positions of the reaction products can be established, preferably by using apparatus operable to detect the labels. Such apparatus may employ laser technology to detect the labels in a conventional manner.

Once the position of the reaction products have been established, they can be calibrated or standardised to take into account varying parameters such as the type of label used, temperature etc., and then compared, by computer with known patterns. The differences in the less conserved intervening sequences will cause the reaction products of different sequences to move through the separating gel at different rates, as a result of differences in size, charge, etc. It is therefore possible to distinguish between different sequences, to an accuracy of one base difference, as in the fluorescence-based PCR single strand conformation polymorphism analysis (PCR-SSCP) [Ellison et al, BioTechniques, Vol 15 No 4 (1993) p684; and Ellison et al, BioTechniques, Vol 17 No 4, 1994, p 742], and hence to distinguish and identify the sequence and source organism in this way.

If the procedure results in a pattern which does not compare with a known pattern, the investigator is still alerted to the presence of an organism, which can then be further investigated by other procedures.

A preferred method of characterising the amplification reaction products involves use of the system marketed by Perkin Elmer under the trademark TaqMan. This is a PCR assay system that uses the hydrolysis of a fluorogenic probe to monitor the extent of amplification. The probe consists of an oligonucleotide labelled with both a fluorescent reporter and a quencher dye. During the PCR process, this probe is cleaved by the 5' nuclease activity of taq DNA polymerase if and only if it hybridises to the segment being amplified. Cleavage of the probe generates an increase in the fluorescence intensity of the reporter dye. Thus, amplification of a specific product can be detected by simply measuring fluorescence after PCR. A separate probe is required for each bacterial or other species to be investigated. But once synthesised, the probes are very quick and easy to use.

As previously mentioned, an improved method of amplifying and identifying a nucleotide sequence comprises using a primer set of at least three cooperable primers to amplify the sequence and at least one portion thereof. The primers of the primer set are preferably the three universal primers as described above. However, it is to be appreciated that the improved method is operable with non-universal primers, for example to increase the fidelity of the PCR-SSCP analysis mentioned above.

The improved method likewise increases the specificity and fidelity of the characterisation and identification methods using the universal primer set described above.

Generally conventional PCR methodology is employed to simultaneously amplify different parts of the sequence using these primers. Two principal reaction products are produced, one between the front and back primers, and one between either the middle and back primers or the front and middle primers depending on which of the middle primers is used.

Thus two different distinguishable sets of reaction products are produced for each sequence amplified. Therefore, the gel pattern produced by separation of these is likely to be more specific and therefore more distinguishable for a given sequence and hence organism than a gel pattern of reaction products produced using only one primer pair.

Each of the reaction products can have a different label to enable them to be identified on the gel.

It is to be appreciated that use of three primers, or more would be in accordance with the present invention. Indeed the more primers that were used, the greater the fidelity and specificity of the technique. The use of four primers is envisaged, where front and back primers plus two middle primers as described above are used. In this case, the two middle primers will be of opposite sense but each will correspond to a different part of the conserved region to avoid formation of primer dimers.

Using the present invention, the investigator can readily resolve the general question, "What is present?", rather than ask the specific question "Is organism X present?".

The invention therefore provides a considerably simpler and more efficient means to identify nucleotide sequences and source organisms in biological samples.

It is to be appreciated that proteins other than the cold shock proteins (and related proteins) may comprise suitable highly conserved regions appropriate for producing universal primers, and that the present invention extends to primer pairs, sets and methods suitable for use in relation thereto. For example, ribosomal proteins, sigma subunits and RsmA comprise regions that appear highly conserved throughout a range of sources, and therefore would appear to provide appropriate sites for suitable universal primers.

Moreover, universal primers may be used in reactions other than PCR.

We claim:

1. A method of identifying the biological source of a nucleic acid sequence in a biological sample, which method comprises using at least one pair of oligonucleotide primers to amplify the nucleic acid sequence, and characterising the amplification reaction products to indicate the biological source of the nucleic acid sequence, wherein the or each pair of oligonucleotide primers hybridises to a sequence that codes for a major cold-shock protein or a eukaryotic Y-box protein and is operable to enable the amplification of nucleic acid sequences from different biological sources, and wherein one primer is complementary to a nucleic acid sequence that codes for the peptide sequence GXVKW-FNXXKGFGFI (SEQ ID No. 1) where X is any amino acid, or for a fragment thereof that includes at least four contiguous identified amino acids.

2. A method as claimed in claim 1, wherein the amplification is performed by the polymerase chain reaction.

3. A method as claimed in claim 1 or claim 2, wherein the characterising is performed by sequencing or by single-strand conformation polymorphism analysis or by the use of a labelled probe which binds to the amplification reaction products.

4. A method as claimed in claim 1, wherein another oligonucleotide primer used is complementary to a nucleic acid sequence that codes for the peptide sequence GPXAX-NVTXX (SEQ ID NO: 3) where X is any amino acid, or for a fragment thereof that includes at least four contiguous identified amino acids.

5. A method as claimed in claim 1, wherein the oligonucleotide primer used has the sequence GGTANAG-TAAAATGGTTNAACNC (SEQ ID NO: 2) where N is any nucleotide, or a fragment thereof containing at least twelve contiguous nucleotides.

6. A method as claimed in claim 4, wherein the oligonucleotide primer used has the sequence GGTTACGT- TANCNGCTNNNGGNCC (SEQ ID NO: 4) where N is any nucleotide, or a fragment thereof containing at least twelve contiguous nucleotides.

7. A method as claimed in claim 5, wherein another oligonucleotide primer used has the sequence GATGTAT-TCGTACATTTCTCTGCTATCC (SEQ ID NO: 6) or its reverse complement GGATAGCAGAGAAATGTAC-GAATACATC (SEQ ID NO: 7) or a fragment of either containing at least twelve contiguous nucleotides.

8. A pair of oligonucleotide primers, operable to enable the amplification of nucleic acid sequences from different biological sources, comprising a first oligonucleotide primer complementary to a nucleic acid sequence that codes for the peptide sequence GXVKWFNXXKGFGFI (SEQ ID NO: 1) where X is any amino acid, or for a fragment thereof that includes at least four contiguous identified amino acids, and another oligonucleotide primer complementary to a nucleic acid sequence that codes for the peptide sequence GPXAX-NVTXX (SEQ ID NO: 3) where X is any amino acid, or for a fragment thereof that includes at least four contiguous identified amino acids.

9. A set of oligonucleotide primers, operable to enable the amplification of nucleic acid sequences from different biological sources, comprising a first oligonucleotide primer having the sequence GGTANAGTAAAATGGTTNAACNC (SEQ ID NO: 2) where N is any nucleotide, or a fragment thereof containing at least twelve contiguous nucleotides, and at least one other oligonucleotide primer having a sequence selected from the group consisting of (i) GGT-TACGTTANCNGCTNNNGGNCC (SEQ ID NO: 4) where N is any nucleotide, or a fragment thereof containing at least twelve contiguous nucleotides and (ii) GATGTATTCGTA-CATTTCTCTGCTATCC (SEQ ID NO: 6) or its reverse complement GGATAGCAGAGAAATGTACGAATACATC (SEQ ID NO: 7) or a fragment of either containing at least twelve contiguous nucleotides.

10. A kit for identifying the biological source of a nucleic acid sequence in a biological sample by the method of claim 1, which kit comprises at least one pair of oligonucleotide primers operable to enable the amplification of nucleic acid sequences from different biological sources, and wherein one primer is complementary to a nucleic acid sequence that codes for the peptide sequence GXVKWFNXXKGFGFI (SEQ ID No. 1) where X is any amino acid, or for a fragment thereof that includes at least four contiguous identified amino acids.

11. A kit as claimed in claim 10, wherein the at least one pair of oligonucleotide primers is a pair of oligonucleotide primers, operable to enable the amplification of nucleic acid sequences from different biological sources, comprising a first oligonucleotide primer complementary to a nucleic acid sequence that codes for the peptide sequence GXVKW-FNXXKGFGFI (SEQ. ID NO: 1) where X is any amino acid, or for a fragment thereof that includes at least four contiguous identified amino acids, and another oligonucleotide primer complementary to a nucleic acid sequence that codes for the peptide sequence GPXAXNVTXX (SEQ ID NO: 3) where X is any amino acid, or for a fragment thereof that includes at least four contiguous identified amino acids.

12. A method as claimed in claim 6, wherein another oligonucleotide primer used has the sequence GATGTAT-TCGTACATTTCTCTGCTATCC (SEQ ID NO: 6) or its reverse complement GGATAGCAGAGAAATGTAC-GAATACATC (SEQ ID NO: 7) or a fragment of either containing at least twelve contiguous nucleotides.

13. A kit as claimed in claim 10, wherein the at least one pair of oligonucleotide primers is a set of oligonucleotide primers, operable to enable the amplification of nucleic acid sequences from different biological sources, comprising a first oligonucleotide primer having the sequence GGTANA-GTAAAATGGTTNAACNC (SEQ ID NO: 2) where N is any nucleotide, or a fragment thereof containing at least twelve contiguous nucleotides, and at least one other oligonucleotide primer having a sequence selected from the group consisting of (i) GGTTACGTTANCNGCTNNNGGNCC (SEQ ID NO: 4) where N is any nucleotide, or a fragment thereof containing at least twelve contiguous nucleotides and (ii) GATGTATTCGTACATTTCTCTGCTATCC (SEQ ID NO: 6) or its reverse complement GGATAGCA-GAGAAATGTACGAATACATC (SEQ ID NO: 7) or a fragment of either containing at least twelve contiguous nucleotides.

14. A kit as claimed in claim 10, comprising a labelled oligonucleotide probe for characterising the amplification reaction products.

15. The method according to claim 1, which comprises the step of identifying the presence of one or more organisms in a biological sample.

16. The method according to claim 1, wherein the different biological sources are different species of an organism.

17. The method according to claim 16, wherein the different biological sources are different species of bacteria.

* * * * *